(12) United States Patent
Haroutunian

(10) Patent No.: US 8,371,291 B2
(45) Date of Patent: Feb. 12, 2013

(54) FLOW MODIFICATION DEVICE

(76) Inventor: G. Greg Haroutunian, Salt Lake City, UT (US)

( * ) Notice: Subject to any disclaimer, the term of this patent is extended or adjusted under 35 U.S.C. 154(b) by 872 days.

(21) Appl. No.: 11/975,592

(22) Filed: Oct. 19, 2007

(65) Prior Publication Data

US 2008/0092888 A1 Apr. 24, 2008

Related U.S. Application Data

(60) Provisional application No. 60/853,347, filed on Oct. 19, 2006.

(51) Int. Cl.
*B05B 1/26* (2006.01)

(52) U.S. Cl. .................. 128/200.18; 128/200.14

(58) Field of Classification Search .......... 128/200.14–200.19, 200.21–200.23, 128/203.15, 203.21, 203.22; 137/561 A, 137/561 R; 138/39, 115, 116; 239/428.5
See application file for complete search history.

(56) References Cited

U.S. PATENT DOCUMENTS

| | | | | |
|---|---|---|---|---|
| 2,906,463 A * | 9/1959 | Curry | ............... | 239/338 |
| 3,453,811 A * | 7/1969 | Crowley | .............. | 96/107 |
| 3,502,103 A * | 3/1970 | Verschuur Eke | ......... | 137/565.33 |
| 3,725,186 A * | 4/1973 | Lynch | ............... | 138/42 |
| 3,965,931 A * | 6/1976 | Skobel | ............... | 137/561 A |
| 4,284,496 A * | 8/1981 | Newton | ............. | 209/3.3 |
| 4,690,332 A | 9/1987 | Hughes | | |
| 4,737,288 A * | 4/1988 | Melis et al. | .................. | 210/521 |
| 4,945,929 A * | 8/1990 | Egilmex | .............. | 131/273 |
| 4,972,830 A | 11/1990 | Wong et al. | | |
| 5,178,138 A | 1/1993 | Walstrom et al. | | |
| 5,392,768 A * | 2/1995 | Johansson et al. | ....... | 128/200.14 |
| 5,435,297 A | 7/1995 | Klein | | |
| 5,461,932 A * | 10/1995 | Hall et al. | .............. | 73/861.61 |
| 5,477,849 A | 12/1995 | Fry | | |
| 5,495,985 A * | 3/1996 | Nehm et al. | .............. | 239/428.5 |
| 5,894,995 A | 4/1999 | Mazzei | | |
| 5,904,139 A | 5/1999 | Hauser | | |
| 5,937,908 A * | 8/1999 | Inoshiri et al. | .................. | 138/39 |
| 6,065,472 A * | 5/2000 | Anderson et al. | ......... | 128/203.21 |
| 6,245,243 B1 * | 6/2001 | Meurer | ......................... | 210/802 |
| 6,510,870 B1 * | 1/2003 | Valaszkai et al. | .............. | 138/38 |

(Continued)

FOREIGN PATENT DOCUMENTS

JP 2003-37383 2/2003

OTHER PUBLICATIONS

W.J. Prest, W. F. Raymond, Fractal Magnetism: Structure and 4D Winding, Syzygy Desktop Publications; Mar. 2004; http://geocities.com/syzygywjp/FractalMagneticField.html. pp. 1-4.

(Continued)

*Primary Examiner* — Thomas Barrett
*Assistant Examiner* — Si M Lee
(74) *Attorney, Agent, or Firm* — Thorpe North & Western LLP

(57) ABSTRACT

An air flow device includes a flow passage having opposite ends. The flow passage (30) is divided into a plurality of sequential portions between the ends including an inlet portion (42) extending into the flow passage (30) from an inlet end (34) an outlet portion (36) disposed at the opposite end of the flow passage (30) from the inlet portion (34), and at least one intermediate passage portion (44) between the inlet passage portion and the outlet passage portion. Each of a plurality of divider sets are positioned in a different sequential portion of the passage to divide that passage portion into a predetermined number of additional passages. At least one of the additional passages is smaller than at least one of the preceding passages.

29 Claims, 6 Drawing Sheets

U.S. PATENT DOCUMENTS

Figure 4:
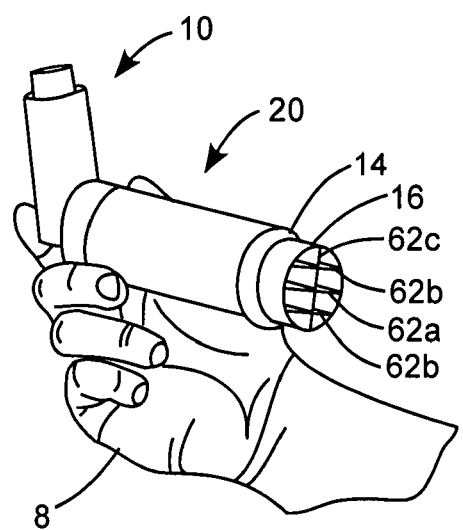

| | | | |
|---|---|---|---|
| 6,606,992 | B1 | 8/2003 | Smith et al. |
| 6,626,169 | B2 | 9/2003 | Gaitini |
| 6,679,250 | B2 * | 1/2004 | Walker et al. ............ 128/200.21 |
| 6,698,422 | B2 | 3/2004 | Fugelsang et al. |
| 6,810,874 | B1 | 11/2004 | Koskela et al. |
| 6,990,974 | B2 * | 1/2006 | Staniforth et al. ....... 128/200.18 |
| 7,781,548 | B2 * | 8/2010 | Fitzgerald et al. .............. 526/88 |
| 2002/0026935 | A1 | 3/2002 | Schmidt et al. |
| 2004/0035412 | A1 | 2/2004 | Staniforth et al. |
| 2004/0216735 | A1 * | 11/2004 | Fugelsang et al. ....... 128/200.23 |
| 2005/0172955 | A1 * | 8/2005 | Sundaram et al. ....... 128/200.23 |
| 2006/0169280 | A1 * | 8/2006 | Yama et al. .............. 128/203.21 |

OTHER PUBLICATIONS

V.S. Ivanova, I.J. Bunin, and V.I. Nosenko, Fractal Material Science: A New Direction in Materials Science, Emerging technologies Overview, Jan. 1998, p. 52.

H J Zar, E G Weinberg, H J Binns, F Gallie, M D Mann, Lung deposition of aerosol-a comparison of different spacers, Arch Dis Child 2000; 82 495-498 (June), p. 1-9.

J P Mitchell, Spacers and holding chambers: Not the last word, we hope, Arch Dis Child 2001; 84:89 (January) p. 1-2.

H J Zar, M Mann, E G Weinberg, Spacers and holding chambers: Not the last word, we hope- a reply, Arch Dis Child 2001; 84:281 (March), p. 1-2.

Harvey Marcovitch, Archives this month, Arch Dis Child 2000; 82: (June); p. 1-4.

Aerochamber Plus; Aerochamber Plus Valved Holding Chamber (VHC) device is the #1 prescribed holding chamber for use with inhaled asthma medications; Forest Laboratories, Inc.; www.frx.com/products/aerochamber.aspx. p. 1-2.

Directions for Use, AeroChamber Plus, 2001,2005 Forest Laboratories, Inc.; 1 page.

AeroChamber Plus has significant advantages compared to the original AeroChamber, AeroChamber Plus Valved Holding Chamber; Product Information; www.aerochambervhc.com/patient/. p. 1-2.

* cited by examiner

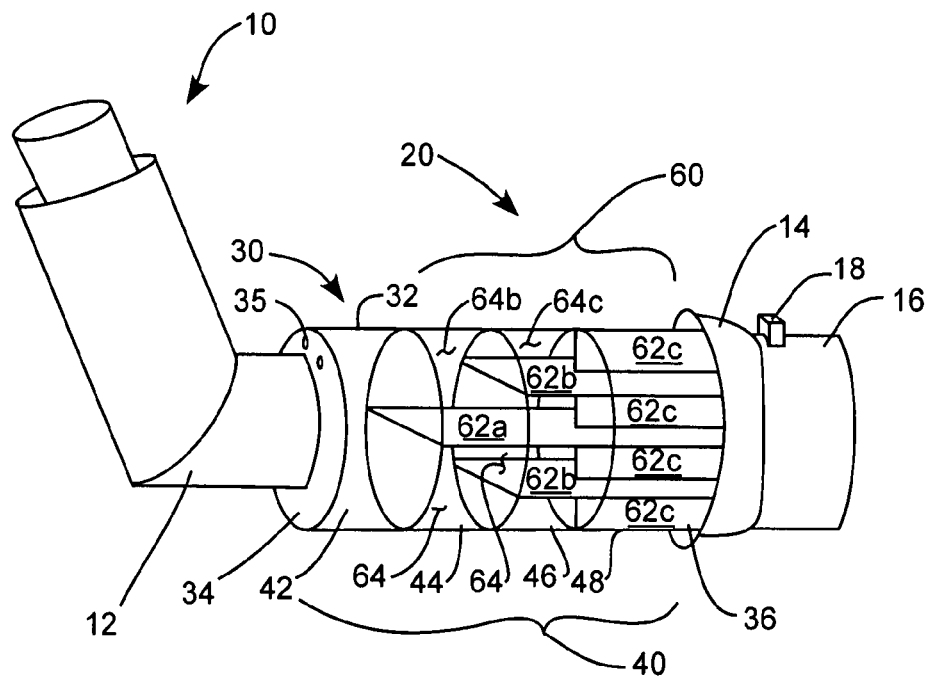
FIG. 1
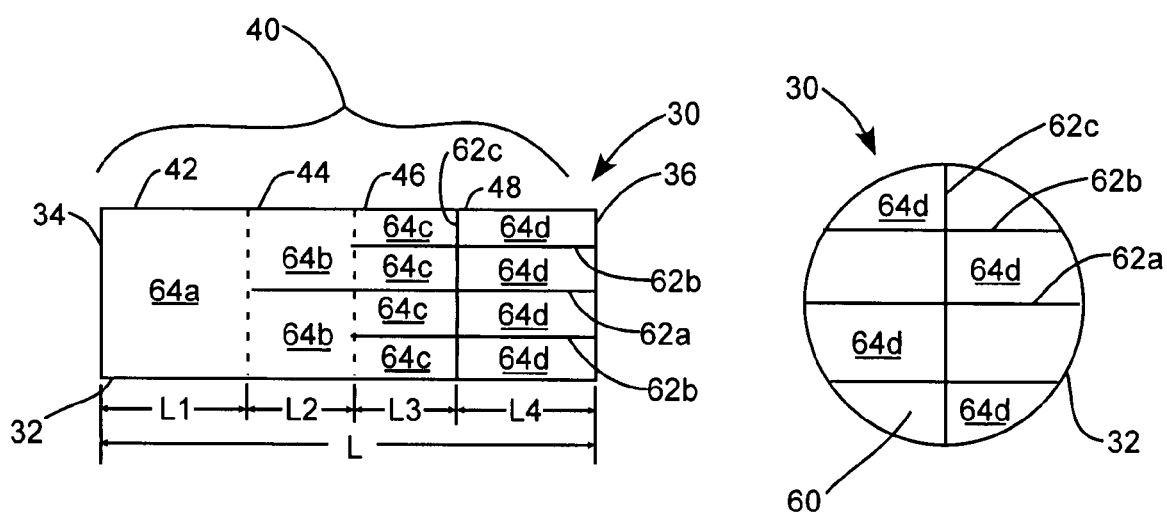
FIG. 2
FIG. 3

FLOW MODIFICATION DEVICE

RELATED APPLICATION

This application claims the benefit of provisional Application Ser. No. 60/853,347, filed Oct. 19, 2006, and entitled "Flow Modification Device", hereby incorporated by reference.

BACKGROUND OF THE INVENTION

1. Field

The invention is in the field of devices to improve the properties of fluid flowing in a passage, particularly fluids containing particles therein. The invention is also in the field of improving the flow properties of an aerosol fluid containing medications prior to inhalation of the fluid by a patient to improve the delivery of the medications through the patient air passages to the lungs.

2. State of the Art

There are many instances where it is desired to lessen turbulence in flowing fluids and create or maintain laminar flow of such fluids. For example, a large number of people suffer from respiratory diseases such as bronchitis, emphysema, and asthma. The symptoms of these diseases in many cases can be reduced by medications inhaled into the lungs by the patient. The medications are typically dispensed from a hand held aerosol dispenser into a housing through which the patient breaths to pull air with the medication droplets therein in through the mouth, down the throat, and into the lungs.

A problem with these treatments is that a major percentage of the medication is deposited in the mouth, throat, and trachea of the patient as the air travels from the mouth to the lungs. With some devices, a significant amount of the medication is also deposited in the device itself, before reaching the mouth. Thus, this medication does not reach the lungs where it is needed, but is wasted and can cause side effects as it contacts and is absorbed by the surfaces of the mouth, throat, and trachea, or as it is swallowed. In many instances, the medication dispenser is a metered dose inhaler set to deliver a specific dose of medication. However, with a major percentage of the medication not reaching the lungs, the dosing is of little value.

While this problem has been recognized in the prior art, most attempts to reduce the problem have focused on ensuring small, uniform medication droplet size (such as uniform droplets in the range of one to three microns) and better and more uniform suspension of the medication droplets in the air to be breathed into the lungs. In many cases this is done by directing the spray of medicine into a spacer or expansion chamber to allow better mixing of the medicine droplets with the air to be breathed prior to breathing of the air. The spacer or chamber also acts as a reservoir to hold the air with medicine therein until breathed by the user, thereby lessening the need for the user to coordinate spraying the medicine with the inhalation of the air containing the medicine.

Spacer devices are often hollow cylindrical, conical, or bottle shaped tubes. One end of the tube has a place where a medicine pump can be attached. The other end of the tube may or may not have a valve, and may or may not have a mask attached. Examples of various spacers or mixing chambers are shown in U.S. Pat. Nos. 4,690,332, 4,972,830, 5,435,297, 5,477,849, and 6,698,422, and the AEROCHAMBER PLUS® product is shown at www.aerochambervhc.com. While providing more uniform, small sized droplets monodispersed into the air to be breathed and providing a reservoir for the air has been found to result in more of the medication reaching the lungs, room for improvement remains.

SUMMARY

The inventor has theorized that at least part of the problem causing deposition of particles suspended in a fluid stream is turbulence in the fluid stream that directs the travel of the particles at angles to the direction of flow of the fluid stream, causing the particles to impact the walls of the flow passages constraining the stream. If turbulence can be reduced, i.e., if more laminar flow of the fluid can be induced, the particles will tend to flow with the stream and the impacting of the particles against the walls defining the flow passage will be reduced. In the particular application to inhalation of aerosol medication, while control of the flow of the air with medication droplets therein is lost once it is inhaled, if a laminar flow with both air and suspended droplets or particles traveling in substantially the same direction at substantially the same speed is provided as the air and medication droplets enter the patient's mouth, the droplets will tend to remain suspended in and travel with the air as it is drawn through the patient's mouth, throat, and trachea, and into the lungs, better than if the droplets are already traveling in various different directions when inhaled. This pre-alignment of air and droplet travel reduces the amount of medicine droplets that will leave the air stream and impact the mouth, throat, and trachea as the air flows to the lungs resulting in more of the medicine actually reaching the lungs.

According to the invention, an air passage, similar to a cylindrical spacer used with an aerosol medicine dispenser, is provided with a plurality of dividers therein to align and guide the flow of air and particles to be inhaled by the patient. This alignment and guidance is provided by sequentially and systematically dividing the initial single flow passage into a larger number of smaller flow passages. This provides a sequential and gradual systematic subdivision of the flow through the passage into multiple smaller flows according to certain rules of subdivision (algorithm). For example, a cylindrical spacer device may form a flow passage extending from an inlet end adapted to receive the outlet of a medication dispenser, such as a metered dose inhaler which produces an aerosol spray of medication droplets at the passage inlet end, and an outlet end to communicate with an air inlet of a patient, such as the patient's mouth. The flow passage may be divided into a plurality of sequential passage portions, with an initial passage portion of preset length forming a single passage adjacent the inlet end. At the end of this initial passage portion, a first intermediate passage portion of preset length may have a divider positioned therein to divide the single passage of the initial portion in half thereby dividing the single passage into two parallel smaller sub flow passages. At the end of the first intermediate portion, a second intermediate portion of preset length may have a divider positioned therein to divide each of the two smaller sub flow passages of the first intermediate portion in half to form four separate parallel smaller sub flow passages. At the end of the second intermediate passage portion, an outlet end passage portion adjacent the outlet end of the passage and of preset length may have a divider positioned therein to divide each of the four sub flow passages of the second intermediate passage portion in half to provide eight parallel smaller sub flow passages. This continued dividing of the passages into smaller passages can continue as desired and as dictated by the overall length of the passage to maintain a laminar flow through the passages which will maintain most of the particles in the fluid and reduce the number of particles impacting the walls of the passage. With the embodiment of the invention directed to use as a spacer for medication inhalation, the first passage portion which is a single passage into which the aerosol medication is sprayed, may be longer than other passage portions and will be dimensioned so as to serve the same purposes of the prior art spacers in providing a reservoir of substantially small medicine droplets suspended in the air to be breathed. The remaining portions of the passage with the dividers therein then act to align and guide the flow of air with medicine droplets therein as the air is breathed in through the passage by the patient to provide a substantially laminar flow of air and droplets into the mouth of the patient.

Figure 5:
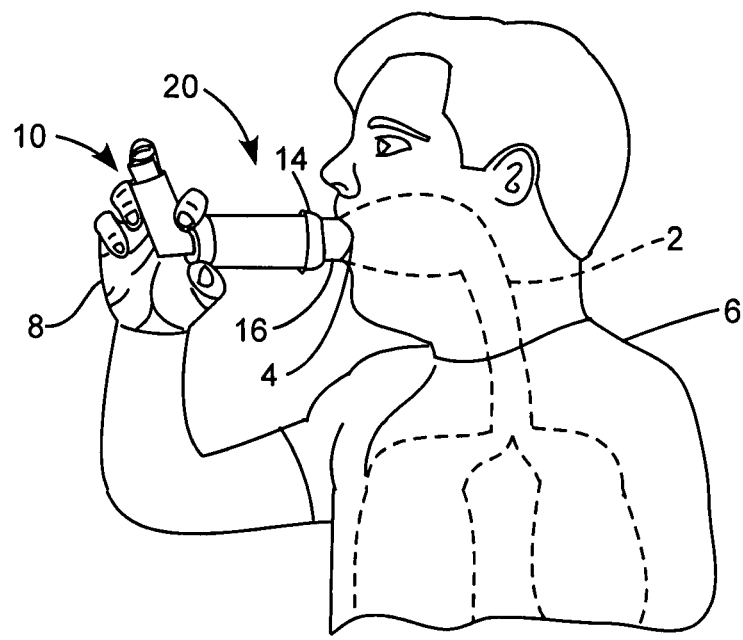

THE DRAWINGS

In the accompanying drawings, which show the best mode currently contemplated for carrying out the invention:

FIG. 1 is a perspective view of an air flow device in accordance with an embodiment of the present invention shown coupled to an aerosolized medication inhaler;

FIG. 2 is a cross-sectional side view of a flow passage of the air flow device of FIG. 1;

FIG. 3 is a cross-sectional end view of a flow passage of the air flow device of FIG. 1;

FIG. 4 is a perspective view of the air flow device of FIG. 1 shown being held in the hand of a patient;

FIG. 5 is a perspective view of the air flow device of FIG. 1 shown directing flow of medicine into the airway of a patient;

FIG. 6 is a perspective view of an air flow device in accordance with another embodiment of the present invention;

FIG. 7 is a perspective view of an air flow device in accordance with another embodiment of the present invention;

FIG. 8 is a perspective view of an air flow device in accordance with another embodiment of the present invention; and FIGS. 9-14 are cross sectional views of a flow passage of an air flow device such as shown in FIG. 1 showing different configurations of partitions dividing the flow passage into sub flow passages.

DETAILED DESCRIPTION OF THE ILLUSTRATED EMBODIMENTS

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The embodiments of the present invention described herein are generally directed to an air passage similar to a cylindrical spacer used with an aerosol medicine dispenser. The air passage is provided with a plurality of divider sets with each divider set positioned sequentially along a length of the air passage. The divider sets align and guide the flow of air and particles to be inhaled by the patient and divide the initial single flow passage into a larger number of smaller flow passages. The divider sets provide a sequential and gradual systematic subdivision of the flow through the passage into multiple smaller flows according to certain rules of subdivision. The rules of subdivision can follow a predetermined geometric progression defined by a mathematical algorithm.

For example, a cylindrical spacer device may form a flow passage extending from an inlet end adapted to receive the outlet of a medication dispenser, such as a metered dose inhaler which produces an aerosol spray of medication droplets at the passage inlet end, and an outlet end to communicate with an air inlet of a patient, such as the patient's mouth. The flow passage may be divided into a plurality of sequential passage portions, with an initial passage portion of preset length forming a single passage adjacent the inlet end. At the end of this initial passage portion, a first intermediate passage portion of preset length may have a divider positioned therein to divide the single passage of the initial portion in half thereby dividing the single passage into two parallel smaller sub flow passages. At the end of the first intermediate portion, a second intermediate portion of preset length may have a divider positioned therein to divide each of the two smaller sub flow passages of the first intermediate portion in half to form four separate parallel smaller sub flow passages. At the end of the second intermediate passage portion, an outlet end passage portion adjacent the outlet end of the passage and of preset length may have a divider positioned therein to divide each of the four sub flow passages of the second intermediate passage portion in half to provide eight parallel smaller sub flow passages. This continued dividing of the passages into smaller passages can continue as desired and as dictated by the overall length of the passage to maintain a laminar flow through the sub flow passages which will maintain the suspension of most of the particles in the fluid and reduce the number of particles impacting the walls of the passage.

With the embodiment of the invention directed to use as a spacer for medication inhalation, the first passage portion, which is a single passage into which the aerosol medication is sprayed, may be longer than other passage portions and will be dimensioned so as to serve the same purposes of the prior art spacers in providing a reservoir of substantially small medicine droplets suspended in the air to be breathed. The remaining portions of the passage with the dividers therein then act to align and guide the flow of air with medicine droplets therein as the air is breathed in through the passage by the patient to provide a substantially laminar flow of air and droplets into the mouth of the patient.

Accordingly, as illustrated in FIGS. 1-3, an air flow device, indicated generally at 20, is shown in accordance with an embodiment of the present invention for providing and maintaining laminar flow of a fluid and maintaining particle suspension in the fluid during fluid flow. The air flow device includes a flow passage, indicated generally at 30, and a plurality of divider sets, indicated generally at 60, sequentially positioned within the flow passage.

In one aspect, the flow passage 30 is formed by a tube 32 having a substantially cylindrical shape. The tube 32 has a longitudinal length, designated as L, that is bounded by two ends, an inlet end 34 and an outlet end 36. The inlet end 34 and outlet end 36 are opposite ends of the tube 32 and air flow moves in the direction from the inlet end toward the outlet end. The tube 32 can be formed of a polymeric material such as plastic and may be transparent, translucent, or opaque.

In one embodiment, the air flow device 20 is directed to use as a spacer for medication inhalation, such as a pressurized metered dose inhaler, as is commonly used to treat asthma or other respiratory ailments. In this embodiment, the flow passage 30 acts as a spacer structure, similar to inhaler spacers as known in the art. The inlet end 34 is adapted to receive the outlet 12 of a medication dispenser, indicated generally at 10, such as an asthma inhaler that can be held in a patient's hand 8, as shown in FIG. 4. The outlet end 36 has an adapter 14 to communicate with an air inlet of a patient 6, such as the patient's mouth 4. In this embodiment, fluid, such as air mixed with medicine, flows through the flow passage 30 of the spacer from the inlet end 34 toward the outlet end 36 and into the patient's airway when the patient breathes in. Thus, the patient sucks the medicine from the spacer into the patient's airway, as shown in FIG. 5. Generally, the connection between the outlet 12 of the medication dispenser 10 and the inlet end 34 of the air flow device 20 is not air tight so that air can flow into the inlet end 34 of the air flow device 20 as the patient sucks the air and medicine through the air flow device. If necessary for relatively free air flow, holes 35 can be provided in the inlet end 34.

Referring again to FIGS. 1-3, a mouthpiece 16 is coupled to the air flow device 20 at the outlet end 36. The mouthpiece is sized and shaped to fit into a patient's mouth 4 and to facilitate delivery of fluid from the air passage 30 to the patient's airway 2. Also, while the mouthpiece 16 is sized and shaped to fit into a patient's mouth 4, it is also sized and shaped, along with adapter 14, to maintain as much as possible the laminar flow created by the air flow device 20 as the air and medication flows from the outlet end 36 of the air flow device 20, through the adapter 14 and mouthpiece 16, and into the patient's mouth 4.

Additionally, a valve 18 can be coupled to the air flow device 20 to restrict fluid movement through the flow passage 30 until desired by the user. The valve 18 can be configured to allow flow of fluid through the flow passage only in a direction from inlet end to outlet end. It will be appreciated that pressurized metered dose inhalers disperse aerosolized medicine into the air which is then inhaled by the patient. It is often desirable for the aerosolized medicine to have time to thoroughly mix with the surrounding air prior to being inhaled so as to ensure a substantially uniform dispersal of medicine throughout the inhaled air in order to maximize the effectiveness of the medicine. Advantageously, the valve 18 keeps the air and medicine in the flow passage 30 until the valve is opened. In this way, the medicine can be allowed to thoroughly mix with the air prior to being inhaled by the patient.

The flow passage 30 is divided into a plurality of sequential portions, indicated generally at 40, between the inlet end 34 and the outlet end 36. In one embodiment, the sequential portions 40 include an inlet portion 42 extending into the flow passage 30 from the inlet end 34 and an outlet portion 48 disposed at the opposite end of the flow passage from the inlet portion 42. Additionally, the flow passage 30 includes at least one intermediate passage portion between the inlet portion 42 and the outlet portion 48. In one aspect, the flow passage 30 can include a first intermediate portion 44 and a second intermediate portion 46.

The plurality of divider sets 60 are positioned inside the tube 32 with each divider set positioned in a different sequential portion of the flow passage 30 so as to divide that portion of the flow passage into a predetermined number of additional sub flow passages 64*a*, 64*b*, 64*c*, and 64*d*. The plurality of divider sets 60 includes partitions 62*a*, 62*b*, 62*c* and 62*d* that divide the flow passage 30 into the smaller sub flow passages 64*a*, 64*b*, 64*c*, and 64*d*. The partitions 62*a*, 62*b*, 62*c* and 62*d* cross the inside of the tube 32 and extend longitudinally along the tube to the outlet end 36 of the flow passage 30. The partitions 62*a*, 62*b*, 62*c* and 62*d* can be formed of a polymeric material such as plastic and can be transparent, translucent, or opaque.

In one aspect, the partitions 62*a*, 62*b*, 62*c* and 62*d* can be oriented at angles with respect to one another such that the partitions intersect one another to form the sub flow passages 64*a*, 64*b*, 64*c*, and 64*d*. In the embodiment shown in FIG. 1, the partitions 62*a*, 62*b*, 62*c* and 62*d* are oriented parallel and orthogonal to one another to form sub flow passages 64*a*, 64*b*, 64*c*, and 64*d* with straight sides formed by the partitions 62*a*, 62*b*, 62*c* and 62*d* and arcuate or curved sides formed by the cylindrical wall of the tube 32.

Additionally, the divider sets 60 are arranged such that at least one of the subsequent sub flow passages 64*c* is smaller than at least one of the preceding passages 64*b* in the preceding divider set. In this way, the divider sets 60 split the flow passage 30 sequentially into a larger number of sub flow passages 64*a*, 64*b*, 64*c*, and 64*d* progressing from the inlet end 34 of the flow passage to the outlet end 36 of the flow passage.

Thus, the plurality of the sets of dividers 60 partition the flow passage 30 into an increasing number of sub flow passages 64*a*, 64*b*, 64*c*, and 64*d* according to the position of the sequential portion of the flow passage 30 with respect to the outlet end 36. Specifically, the portions of the flow passage 30 closer to the inlet end 34 have fewer sub flow passages 64*a*, 64*b*, 64*c*, and 64*d* and the portions of the flow passage closer to the outlet end 36 have more sub flow passages.

Accordingly, the inlet portion 42 of the flow passage 30 has a preset length, $L_1$, and no dividers so that the inlet portion is a single passage 64*a* adjacent the inlet end 34. It will be appreciated that the length $L_1$ of the inlet portion 42 of the passage 30 is relatively longer than lengths of the subsequent portions 44, 46, and 48 of the flow passage so as to facilitate mixing of the medicine from the inhaler 10 with the air in the flow passage 30 prior to subdividing the passage in subsequent portions of the flow passage.

At the end of the inlet portion 42, a first intermediate passage portion 44 of preset length, $L_2$, has a single divider 62*a* positioned therein which divides the single passage 64*a* of the initial portion 42 in half to form two parallel smaller sub flow passages 64*b* that extend through the first intermediate portion 44. At the end of the first intermediate portion 44, a second intermediate portion 46 of preset length, $L_3$, has another divider 62*b* positioned therein which divides each of the two smaller sub flow passages 64*b* of the first intermediate portion 44 in half to form four separate parallel smaller sub flow passages 64*c* that extend through the second intermediate portion 46. At the end of the second intermediate portion 46, an outlet end portion 48 adjacent the outlet end 36 of the passage 30 and of preset length, $L_4$, has another divider 62*c* positioned therein to divide each of the four sub flow passages 64*c* of the second intermediate portion 46 in half to provide eight parallel smaller sub flow passages 64*d* that extend through the outlet portion 48. In this way, the fluid in the flow passage 30 is aligned and guided from the inlet end 34 of the flow passage to the outlet end 36 of the flow passage.

Additionally, it will be appreciated that the length of each portion of the flow passage 30 can be shorter the closer the portion is to the outlet end 36. Thus, the sub flow passages of each subsequent portion have both a smaller volume and a shorter length than the sub flow passages of the preceding portion.

The subdivision of the flow passage 30 can be determined according to a pre-selected algorithm. In one aspect, the algorithm can conform to a mathematical rule, such as a geometric progression. The algorithm may also take into account the length of the flow, the cross sectional area, and the volume of the flow passage or sub flow passages. For example, the algorithm may predetermine that each new divider subdivides the existing flow passage into two new sub flow passages, as illustrated in FIG. 1. In this case, the ratio of cross sectional areas of the two newly formed sub flow passages in each subsequent portion of the flow passage will be approximately 2:1, and the sum of the cross sectional areas of each individual sub flow passage approximately equals the cross sectional area of the original flow passage. Additionally, the length of the newly formed sub flow passages in each subsequent portion of the flow passage 30 can be approximately $9/10^{th}$ of the preceding sub flow passage. Thus, the algorithm can be used to predetermine a fixed ratio of cross sectional areas and a fixed ratio of lengths for each sub flow passage.

It will be appreciated that other algorithms for subdividing the flow passage 30 can also be used. For example, the concepts of the present invention contemplate algorithms for dividing the flow passage that take into account physical properties of the fluid and/or substance being suspended or mixed with the fluid traveling through the flow path. As another example, a random placement of dividers throughout the flow passage may be desirable and can be used with the flow passage described herein. As yet another example, the algorithm may also predetermine the shape of the flow passage and/or the shape of the dividers in the flow passage. Thus, the algorithm for determining subdivision of the flow passage can be tailored to meet the intended usage of the flow device 10.

It will also be appreciated that the number of passage portions needed to maintain laminar flow, and if particles are suspended in the fluid, to maintain the particles in suspension, will vary with the distance the fluid needs to travel and the particular fluid and, if present, the particular characteristics of the particles. Many shapes of passages and many configurations of dividers to divide the passages into more passages can be used. Usually, the configuration of dividers and lengths of passage portions will be determined by particular formulas or algorithms that have been determined as applicable for the particular situation where the invention is used.

It will be further appreciated that if necessary to help maintain the established laminar flow from the outlet end portion 48 of the device, the dividers from the outlet portion 48 can extend into the adapter 14 and mouthpiece 16 interfacing the outlet end 36 of the device with the patient's mouth 4, as shown in FIG. 4.

Figure 6:
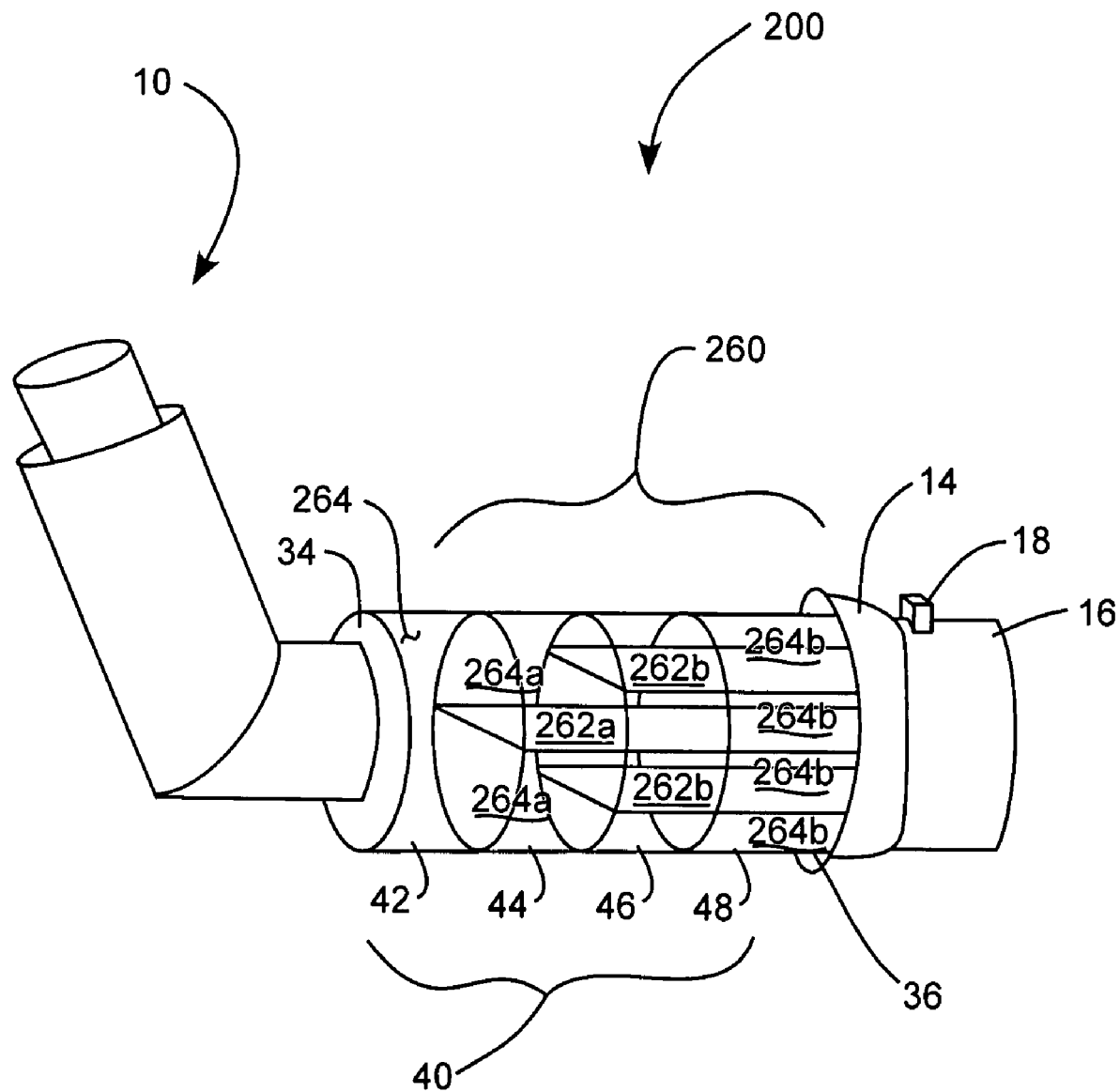

Accordingly, as illustrated in FIG. 6, an air flow device, indicated generally at 200, is shown in accordance with another embodiment of the present invention for providing and maintaining laminar flow of a fluid and maintaining particle suspension in the fluid during fluid flow. The air flow device 200 is similar in many respects to the air flow device 20 described above and shown in FIGS. 1-3. The air flow device includes a flow passage, indicated generally at 30 and a plurality of divider sets, indicated generally at 260, sequentially positioned within the flow passage.

The flow passage 30 has a plurality of sequential portions, indicated generally at 40, including an inlet portion 42 adjacent an inlet end 34, a first intermediate portion 44, a second intermediate portion 46, and an outlet portion 48 adjacent an outlet end 36. The dividers 260 disposed in the flow passage 30 include partitions 262a and 262b that divide the flow passage 30 into sub flow passages 264, 264a and 264b. The partitions 262a and 262b include a central partition 262a positioned in the flow passage 30 after the inlet portion 34 to divide the flow passage into two substantially equal sub flow passages 264a in the first intermediate portion 44. Additional partitions 262b and 262c are positioned in the flow passage 30 after the first intermediate portion 44 to divide each of the sub flow passages 264a in the first intermediate portion into two substantially equal sub flow passages 264b, thereby forming four sub-flow passages 364b in the second intermediate portion 46 and the outlet portion 48. In this embodiment, the portion of the passage with the four sub-flow passages 364b is longer than the portions with the one and two sub-flow passages.

Figure 7:
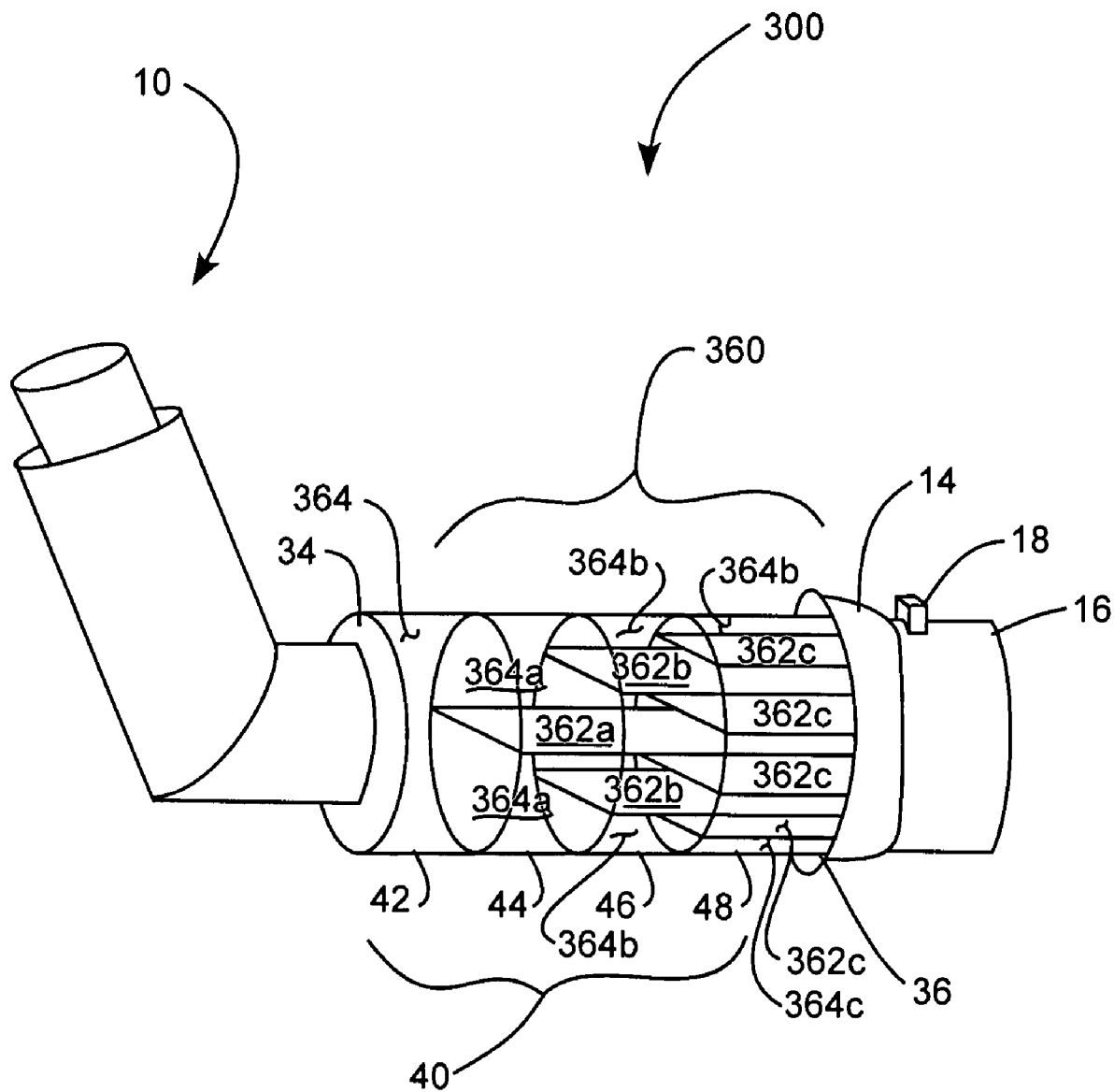

As illustrated in FIG. 7, an air flow device, indicated generally at 300, is shown in accordance with another embodiment of the present invention for providing and maintaining laminar flow of a fluid and maintaining particle suspension in the fluid during fluid flow. The air flow device 300 is similar in many respects to the air flow devices 20 and 200 described above and shown in FIGS. 1-3 and FIG. 6, respectively. The air flow device 300 includes a flow passage, indicated generally at 30 and a plurality of divider sets, indicated generally at 360, sequentially positioned within the flow passage.

The flow passage 30 has a plurality of sequential portions, indicated generally at 40, including an inlet portion 42 adjacent an inlet end 34, a first intermediate portion 44, a second intermediate portion 46, and an outlet portion 48 adjacent an outlet end 36. The dividers 360 disposed in the flow passage 30 include partitions 362 that divide the flow passage 30 into sub flow passages 364. The partitions 362 include a central partition 362a positioned in the flow passage 30 after the inlet portion 34 to divide the flow passage into two substantially equal sub flow passages 364a in the first intermediate portion 44. Additional partitions 362b and 362c are positioned in the flow passage 30 after the first intermediate portion 44 to divide each of the sub flow passages 364a in the first intermediate portion into two substantially equal sub flow passages 364b, thereby forming four sub-flow passages 364b in the second intermediate portion 46. Similarly, additional partitions 362d and 362e are positioned in the flow passage 30 after the second intermediate portion 46 to divide each of the sub flow passages 364b in the second intermediate portion 46 into two substantially equal sub flow passages 364c, thereby forming eight sub-flow passages 364b in the outlet portion 48.

Figure 8:
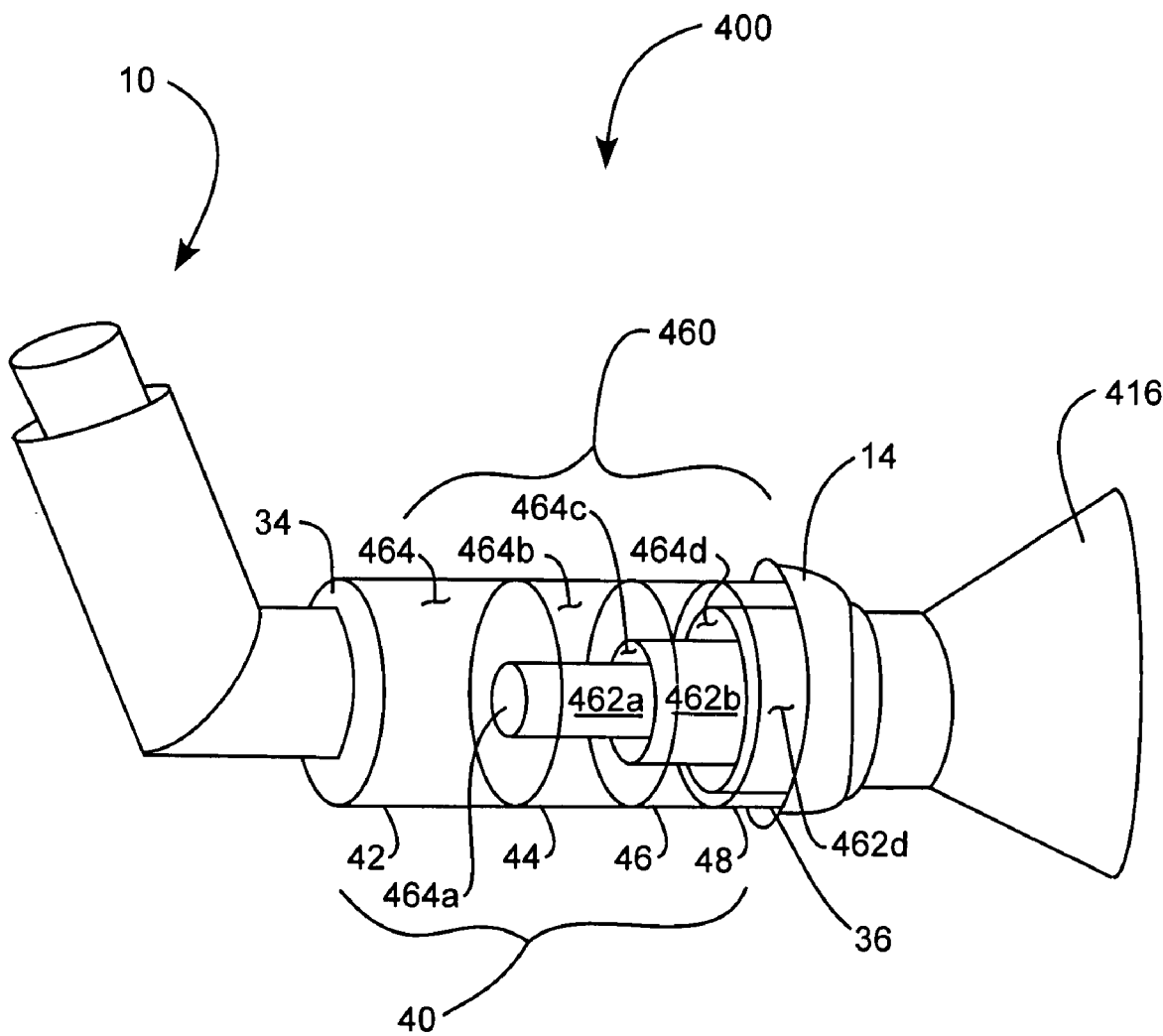

As illustrated in FIG. 8, an air flow device, indicated generally at 400, is shown in accordance with another embodiment of the present invention for providing and maintaining laminar flow of a fluid and maintaining particle suspension in the fluid during fluid flow. The air flow device 400 is similar in many respects to the air flow devices 20, 200, and 300 described above and shown in FIGS. 1-3, FIG. 6, and FIG. 7, respectively. The air flow device 400 includes a flow passage, indicated generally at 30 and a plurality of divider sets, indicated generally at 460, sequentially positioned within the flow passage.

The flow passage 30 has a plurality of sequential portions, indicated generally at 40, including an inlet portion 42 adjacent an inlet end 34, a first intermediate portion 44, a second intermediate portion 46, and an outlet portion 48 adjacent an outlet end 36. The dividers 460 disposed in the flow passage 30 include partitions 462a, 462b, and 462c that divide the flow passage 30 into sub flow passages 464a, 464b, 464c, and 464d. The partitions 462a, 462b, and 462c are cylindrically shaped and divide the flow passage 30 into circular or annular sub flow passages. Specifically, the partitions 462a, 462b, and 462c include a central partition 462a positioned in the flow passage 30 after the inlet portion 34 to divide the flow passage into an inner sub flow passages 464a and an outer sub flow passage 464b in the first intermediate portion 44. An additional partition 462b is positioned in the flow passage 30 after the first intermediate portion 44 to divide the outer sub flow passage 464b in the first intermediate portion 44 into a first intermediate sub flow passage 464c and an outer sub flow passage 464b thereby forming three sub-flow passages in the second intermediate portion 46. Similarly, an additional partition 464c is positioned in the flow passage 30 after the second intermediate portion 46 to divide the outer sub flow passage 464b in the second intermediate portion 46 into a second intermediate sub flow passage 464d and an outer sub flow passage 464b thereby forming four sub-flow passages in the outlet portion 48.

Additionally, a face mask 416 is coupled to the outlet end 48 to facilitate delivery of fluid from the air flow device to the patient's airway. The face mask 416 can be configured to fit over the mouth or the mouth and nose of the patient.

Figure 9:
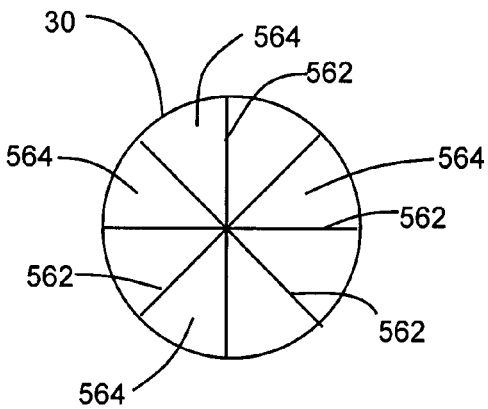
Figure 10:
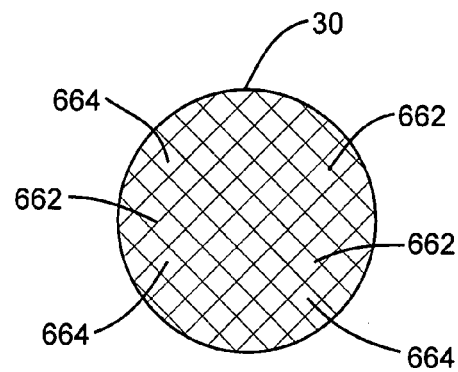
Figure 11:
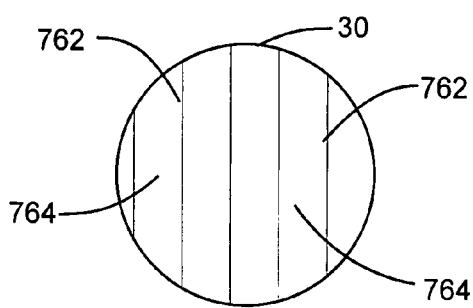
Figure 12:
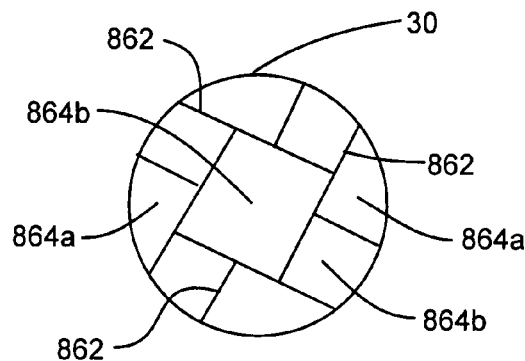
Figure 13:
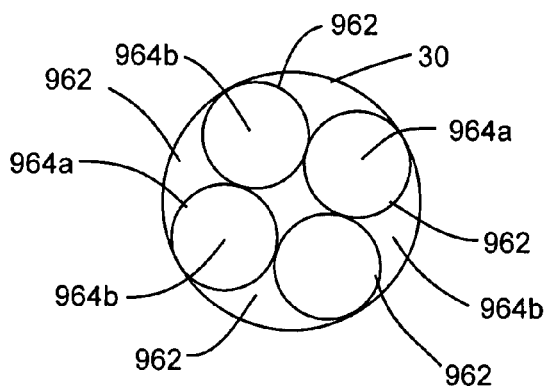
Figure 14:
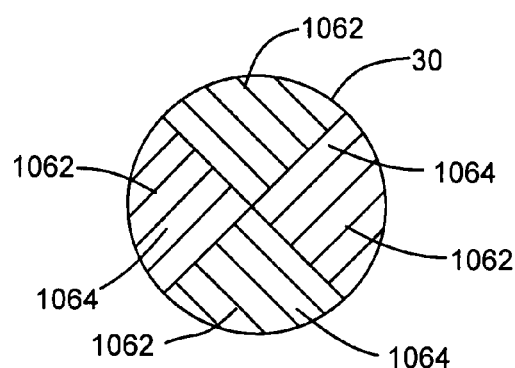

As illustrated in FIGS. 9-14, other divider arrangements are shown for use in an air flow device 20 described above and shown in FIGS. 1-3. FIG. 9 illustrates a cross section of a flow passage 30 with radial partitions 562 dividing the flow passage into wedge shaped sub flow passages 564. FIG. 10 illustrates a cross section of a flow passage 30 with crisscross partitions 662 dividing the flow passage into diamond shaped sub flow passages 664. FIG. 11 illustrates a cross section of a flow passage 30 with substantially vertical and parallel partitions 762 dividing the flow passage into vertical sub flow passages 764. FIG. 12 illustrates a cross section of a flow passage 30 with partitions 862 dividing the flow passage into a patchwork pattern with substantially triangular sub flow passages 864a and quadrangular sub flow passages 864b. FIG. 13 illustrates a cross section of a flow passage 30 with partitions 962 dividing the flow passage into circular sub flow passages 964a and arcuate sub flow passages 964b. FIG. 14 illustrates a cross section of a flow passage 30 with partitions 1062 dividing the flow passage into a mixture of orthogonally oriented segmented sub flow passages 1064.

It will be appreciated that the partitions can divide the flow passage 30 into any number of patterns to facilitate parallel flow, axial flow, radial flow, concentric flow, alternating flow, and the like. Additionally, the partitions can be symmetrically or asymmetrically placed within the flow passage.

The present invention also provides for a method for providing and maintaining laminar flow of a fluid and maintaining particle suspension in the fluid as the fluid flows along a fluid passage including sequentially dividing the flow of fluid in the passage into multiple smaller flows of fluid as the fluid flows along the passage from an inlet portion to an intermediate portion. Additionally, the flow of fluid in the passage can be sequentially divided into smaller flows of fluid as the fluid flows along the passage from the intermediate portion to an outlet portion.

The dividers of the air flow device of the present invention provides several advantages to fluid flow of aerosolized inhalable medicine. For example, it is believed the divider structure in the air passage of the air flow device aligns and guides the aerosolized medicine into the patient's airway, thereby reducing wasted medicine that may contact the sidewalls of traditional spacers. Additionally, it is believed the dividers reduce the turbulence and resistance of fluid flow through the spacer which also results in better medicine delivery. Moreover, the dividers significantly increase the surface area of the lateral walls, which serves to filter out lateral flow through the air passage. In this way, particles of aerosolized medicine that may become stuck on the lateral walls of the patient's airway are eliminated from the flow before they get to the patient's airway. Thus, the embodiments of the air flow devices described herein, provide better and more controlled delivery of the aerosolized medicine to a patient's lungs.

The concepts of the present invention described herein is not limited to use as a spacer for aerosol medicine applicators, but can be used anytime a fluid flows from one point to another point. For example, the dividers 60 of the air flow device 20 can be used to align and guide fluid within the space of an oxygen mask, endotracheal tube, nasal cannulas, and the like, or can be used in various other types of fluid flow passages, pipes, conduits, etc. Additionally, it will be appreciated that the sets of dividers 60 can be positioned or placed within a confined space, such as the cylindrical tube 32 described above, or the dividers 60 can be formed without an external wall such that the dividers can be placed within any existing fluid flow device or structure. In this way, the dividers can be used to improve or enhance various existing air flow passages, and are not limited to existing inhaler spacers.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

The invention claimed is:

1. A device for providing and maintaining laminar flow of a fluid and maintaining particle suspension in the fluid during fluid flow, comprising:
   a) a flow passage having opposite ends, said flow passage being divided into a plurality of equal length connecting sequential portions between the ends, the sequential portions including:
      i) an inlet flow passage portion extending into the flow passage from an inlet end;
      ii) an outlet flow passage portion disposed at the opposite end of the flow passage from the inlet flow passage portion; and
      iii) at least one intermediate flow passage portion between the inlet flow passage portion and the outlet flow passage portion;
      each flow passage portion other than the outlet flow passage portion having a next sequential flow passage portion and each flow passage portion other than the inlet flow passage portion having a next preceding flow passage portion;
   b) a plurality of divider sets, each divider set positioned in a different sequential flow passage portion of the flow passage with one of the plurality of divider sets being positioned in each of the inlet flow passage portion, the outlet flow passage portion, and each of the at least one intermediate flow passage portions to divide each of the flow passage portions into a predetermined number of sub flow passages forming continuations of the sub flow passages of the next preceding flow passage portion;
   c) whereby the flow passage is sequentially divided into an increasing number of the sub flow passages progressing from the inlet portion of the flow passage to the outlet portion of the flow passage and at least one of the sub flow passages of each sequential portion of the flow passage beyond the inlet flow passage portion is divided into a plurality of additional smaller sub flow passages in the next sequential flow passage portion of the flow passage.

2. A device for providing and maintaining laminar flow of a fluid and maintaining particle suspension in the fluid during fluid flow according to claim 1, wherein structure defining the flow passage is substantially cylindrical.

3. A device for providing and maintaining laminar flow of a fluid and maintaining particle suspension in the fluid during fluid flow according to claim 1, wherein each time the flow passage is divided into an increasing number of sub flow passages, each of the sub flow passages of the next preceding flow passage portion are divided into additional smaller sub flow passages.

4. A device for providing and maintaining laminar flow of a fluid and maintaining particle suspension in the fluid during fluid flow according to claim 3, wherein each sequential division of a flow passage portion into a larger number of smaller sub flow passages divides each of the sub flow passages of the next preceding flow passage portion into two smaller sub flow passages.

5. A device for providing and maintaining laminar flow of a fluid and maintaining particle suspension in the fluid during fluid flow according to claim 4, wherein each sequential division of a flow passage portion into a larger number of smaller sub flow passages divides each of the sub passages of the next preceding flow passage portion in half.

6. A device for providing and maintaining laminar flow of a fluid and maintaining particle suspension in the fluid during fluid flow according to claim 1, wherein each sequential division of a flow passage portion into a larger number of smaller sub flow passages divides the sub passages of the next preceding flow passage portion into additional smaller sub flow passages according to a predetermined formula.

7. A device for providing and maintaining laminar flow of a fluid and maintaining particle suspension in the fluid during fluid flow according to claim 1, wherein the device forms a spacer structure for an inhaler device for delivery of medication to a patient, wherein the inlet end is adapted to receive the outlet of a medication dispenser, and the outlet end is adapted to communicate with an air inlet of a patient.

8. A device for providing and maintaining laminar flow of a fluid and maintaining particle suspension in the fluid during fluid flow according to claim 7, wherein each time the flow passage is divided into an increasing number of sub flow passages, each sub flow passage of the next preceding flow passage portion is divided into additional smaller sub flow passages.

9. A device for providing and maintaining laminar flow of a fluid and maintaining particle suspension in the fluid during fluid flow according to claim 8, wherein each sequential division of a flow passage portion into a larger number of smaller sub flow passages divides each sub flow passage of the next preceding flow passage portion into two smaller sub flow passages.

10. A device for providing and maintaining laminar flow of a fluid and maintaining particle suspension in the fluid during fluid flow according to claim 7, wherein the outlet end is configured as a mouthpiece to communicate with the mouth of a patient.

11. A device for providing and maintaining laminar flow of a fluid and maintaining particle suspension in the fluid during fluid flow according to claim 7, wherein the inlet end is adapted to receive the outlet of a pressurized metered dose inhaler.

12. A device for providing and maintaining laminar flow of fluid and maintaining particle suspension in the fluid during fluid flow according to claim 11, wherein the inlet end of the flow passage, in addition to being adapted to receive the outlet of a medication dispenser, includes openings to allow atmospheric air flow into the inlet end of the flow passage.

13. A device for providing and maintaining laminar flow of a fluid and maintaining particle suspension in the fluid during fluid flow according to claim 7, wherein the flow passage portion adjacent the inlet end forms a single flow passage.

14. A device for providing and maintaining laminar flow of a fluid and maintaining particle suspension in the fluid during fluid flow according to claim 7, wherein the spacer structure is substantially cylindrical.

15. A device for providing and maintaining laminar flow of fluid and maintaining particle suspension in the fluid during fluid flow according to claim 7, wherein the inlet end of the flow passage, in addition to being adapted to receive the outlet of a medication dispenser, includes openings to allow atmospheric air flow into the inlet end of the flow passage.

16. A device for providing and maintaining laminar flow of fluid and maintaining particle suspension in the fluid during fluid flow according to claim 7, wherein each flow passage portion provides a total flow passage cross sectional area, and wherein the total flow passage cross sectional area of each flow passage portion is approximately equal.

17. A device for providing and maintaining laminar flow of a fluid and maintaining particle suspension in the fluid during fluid flow according to claim 1, wherein each flow passage portion provides a total flow passage cross sectional area, and wherein the total flow passage cross sectional area of each flow passage portion is approximately equal.

18. A device for providing and maintaining laminar flow of a fluid and maintaining particle suspension in the fluid during fluid flow according to claim 1, wherein each divider set is positioned with respect to the divider set in the next preceding flow passage portion to prevent flow communication between sub flow passages of the next preceding flow passage portion.

19. A device for providing and maintaining laminar flow of a fluid and maintaining particle suspension in the fluid during fluid flow according to claim 1, wherein structure defining the flow passage a substantially straight elongate tubular structure.

20. A device for providing and maintaining laminar flow of a fluid and maintaining particle suspension in the fluid during fluid flow, comprising:

a) an elongate tubular structure forming a flow passage therethrough having opposite ends, said flow passage being divided into four connecting sequential flow passage portions between the ends, the sequential portions including:

i) an inlet flow passage portion extending into the flow passage from an inlet end;

ii) an outlet flow passage portion disposed at the opposite end of the flow passage from the inlet flow passage portion; and iii) two intermediate flow passage portions between the inlet flow passage portion and the outlet flow passage portion;

each flow passage portion other than the outlet flow passage portion having a next sequential flow passage portion and each flow passage portion other than the inlet flow passage portion having a next preceding flow passage portion;

b) a plurality of divider sets, each divider set positioned in a different sequential flow passage portion of the flow passage to divide that flow passage portion into a predetermined number of sub flow passages forming continuations of the sub flow passages of the next preceding flow passage portion;

c) whereby the flow passage is sequentially divided into an increasing number of the sub flow passages progressing from the inlet portion of the flow passage to the outlet portion of the flow passage and at least one of the sub flow passages of each sequential portion of the flow passage beyond the inlet flow passage portion is divided into a plurality of additional smaller sub flow passages in the next sequential flow passage portion of the flow passage, wherein the inlet end forms a single flow passage, and the flow passage portion adjacent the outlet end forms eight sub flow passages, and wherein the device forms a spacer structure for an inhaler device for delivery of medication to a patient, wherein the inlet end is adapted to receive the outlet of a medication dispenser, and the outlet end is adapted to communicate with an air inlet of a patient.

21. A device for providing and maintaining laminar flow of a fluid and maintaining particle suspension in the fluid during fluid flow according to claim 20, wherein each sequential flow passage portion is of equal length.

22. A device for providing and maintaining laminar flow of a fluid and maintaining particle suspension in the fluid during fluid flow according to claim 20, wherein each sequential flow passage portion is of a length determined by a predetermined formula.

23. A device for providing and maintaining laminar flow of a fluid and maintaining particle suspension in the fluid during fluid flow according to claim 20, wherein the outlet end is configured as a mouthpiece to communicate with the mouth of a patient.

24. A device for providing and maintaining laminar flow of a fluid and maintaining particle suspension in the fluid during fluid flow according to claim 20, wherein the inlet end is adapted to receive the outlet of a pressurized metered dose inhaler.

25. A device for providing and maintaining laminar flow of a fluid and maintaining particle suspension in the fluid during fluid flow according to claim 20, wherein the spacer structure is substantially cylindrical.

26. A device for providing and maintaining laminar flow of a fluid and maintaining particle suspension in the fluid during fluid flow according to claim 20, wherein the elongate tubular structure is a substantially straight elongate tubular structure.

27. A device for providing and maintaining laminar flow of fluid and maintaining particle suspension in the fluid during fluid flow according to claim 20, wherein the inlet end of the flow passage, in addition to being adapted to receive the outlet of a medication dispenser, includes openings to allow atmospheric air flow into the inlet end of the flow passage.

28. A device for providing and maintaining laminar flow of fluid and maintaining particle suspension in the fluid during fluid flow according to claim 20, wherein each flow passage portion provides a total flow passage cross sectional area, and wherein the total flow passage cross sectional area of each flow passage portion is approximately equal.

29. A device for providing and maintaining laminar flow of a fluid and maintaining particle suspension in the fluid during fluid flow according to claim 20, wherein each divider set is positioned with respect to the divider set in the next preceding flow passage portion to prevent flow communication between sub flow passages of the next preceding flow passage portion.

\* \* \* \* \*